US00PP19223P2

(12) United States Plant Patent
Takayoshi

(10) Patent No.: US PP19,223 P2
(45) Date of Patent: Sep. 16, 2008

(54) ***COSMOS* PLANT NAMED 'NEW CHOCO'**

(50) Latin Name: *Cosmos atrosanguineus*
Varietal Denomination: New Choco

(75) Inventor: Oku Takayoshi, Iga Mie (JP)

(73) Assignee: Osco Garden B.V., De Kwakel (NL)

( * ) Notice: Subject to any disclaimer, the term of this patent is extended or adjusted under 35 U.S.C. 154(b) by 0 days.

(21) Appl. No.: 11/974,215

(22) Filed: Oct. 11, 2007

(51) Int. Cl.
*A01H 5/00* (2006.01)

(52) U.S. Cl. ..... Plt./418

(58) Field of Classification Search ..... Plt./418
See application file for complete search history.

*Primary Examiner*—Annette H Para
(74) *Attorney, Agent, or Firm*—C. A. Whealy

(57) ABSTRACT

A new and distinct cultivar of *Cosmos* plant named 'New Choco', characterized by its upright and outwardly spreading plant habit; freely branching growth habit; freely flowering habit; single type inflorescences with intense red-colored ray florets; relatively tolerant to Powdery Mildew; and good garden performance.

1 Drawing Sheet

Botanical designation: *Cosmos atrosanguineus.*
Cultivar denomination: 'New Choco'.

BACKGROUND OF THE INVENTION

The present invention relates to a new and distinct cultivar of *Cosmos* plant, botanically known as *Cosmos atrosanguineus* and hereinafter referred to by the name 'New Choco'.

The objective of the breeding program is to create new *Cosmos* cultivars that are less susceptible to Powdery Mildew and more tolerant to high temperatures.

The new *Cosmos* originated from an open-pollination in June, 2002 In Iga Mie, Japan of an unnamed seedling selection of *Cosmos atrosanguineus,* not patented, as the female, or seed, parent with an unidentified selection of *Cosmos atrosanguineus,* as the male, or pollen, parent. The new *Cosmos* was discovered and selected by the Inventor as a single flowering plant within the progeny of the stated open-pollination in a controlled environment in Iga Mie, Japan in June, 2003.

Asexual reproduction of the new *Cosmos* by vegetative cuttings was first conducted in Iga Mie, Japan in June, 2004. Asexual reproduction by cuttings has shown that the unique features of this new *Cosmos* are stable and reproduced true to type in successive generations.

SUMMARY OF THE INVENTION

Plants of the cultivar New Choco have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'New Choco'. These characteristics in combination distinguish 'New Choco' as a new and distinct potted *Cosmos* cultivar:

1. Upright and outwardly spreading plant habit.
2. Freely branching growth habit.
3. Freely flowering habit.

4. Single type inflorescences with intense red-colored ray florets.
5. Relatively tolerant to Powdery Mildew.
6. Good garden performance.

Plants of the new *Cosmos* differ from plants of the female parent selection in the following characteristics:

1. Plants of the new *Cosmos* root faster than plants of the female parent selection.
2. Plants of the new *Cosmos* are more freely branching than plants of the female parent selection.
3. Plants of the new *Cosmos* and the female parent selection differ in ray floret coloration.
4. Plants of the new *Cosmos* are more tolerant to rain and high temperatures than plants of the female parent selection.
5. Plants of the new *Cosmos* are more tolerant to Powdery Mildew than plants of the female parent selection.

Plants of the new *Cosmos* can be compared to plants of the *Cosmos* cultivar Strawberry Choco Sanse 41, disclosed in U.S. Plant Pat. No. 16,966. In side-by-side comparisons conducted in De Kwakel, The Netherlands, plants of the new *Cosmos* differed from plants of the cultivar Strawberry Choco Sanse 41 in the following characteristics:

1. Plants of the new *Cosmos* were more compact than plants of the cultivar Strawberry Choco Sanse 41.
2. Plants of the new *Cosmos* and the cultivar Strawberry Choco Sanse 41 differed in leaf, inflorescence bud and ray floret color.

BRIEF DESCRIPTION OF THE PHOTOGRAPHS

The accompanying photographs illustrate the overall appearance of the new *Cosmos.* These photographs show the colors as true as it is reasonably possible to obtain in colored reproductions of this type. Colors in the photographs may differ slightly from the color values cited in the detailed botanical description which accurately describe the colors of the new *Cosmos.*

The photograph at the top of the sheet comprises a side perspective view of a typical flowering plant of 'New Choco' grown in a container.

The photograph in the middle of the sheet is a close-up view of a typical inflorescence of 'New Choco'.

The photograph at the bottom of the sheet is a close-up view of typical leaves of 'New Choco'.

DETAILED BOTANICAL DESCRIPTION

The aforementioned photographs and following observations and measurements describe plants grown during the winter and spring in De Kwakel, The Netherlands in a glass-covered greenhouse and under conditions and practices which approximate those generally used in commercial potted *Cosmos* production. During the production of the plants, day temperatures averaged 16° C. and night temperatures averaged 13° C. Plants were pinched one time. Plants used in the photographs and for the description were pinched one time and were about six months old. In the following description, color references are made to The Royal Horticultural Society Colour Chart, 2001 Edition, except where general terms of ordinary dictionary significance are used.

Botanical classification: *Cosmos atrosanguineus* cultivar New Choco.

Parentage:

*Female, or seed, parent.*—Unnamed seedling selection of *Cosmos atrosanguineus,* not patented.

*Male, or pollen, parent.*—Unidentified selection of *Cosmos atrosanguineus,* not patented.

Propagation:

*Type.*—Vegetative cuttings.

*Time to initiate roots, summer.*—About ten days at temperatures of about 20° C. to 36° C.

*Time to initiate roots, winter.*—About two weeks at temperatures of about 13° C. to 20° C.

*Time to produce a rooted young plant, summer.*—About three weeks at temperatures of about 20° C. to 36° C.

*Time to produce a rooted young plant, winter.*—About four weeks at temperatures of about 13° C. to 20° C.

*Root description.*—Medium in thickness, fleshy; white in color.

*Rooting habit.*—Freely branching; dense.

Plant description:

*Appearance.*—Upright and outwardly spreading plant habit; relatively compact. Freely branching growth habit with about 13 lateral branches developing per plant; pinching enhances lateral branch development. Moderately vigorous to vigorous growth habit.

*Plant height.*—About 44.6 cm.

*Plant width.*—About 70 cm.

*Lateral branches.*—Length: About 33.4 cm. Diameter: About 4.5 mm. Internode length: About 5.5 cm. Strength: Moderately strong; young stems, flexible. Texture: Densely pubescent. Color: Between N186C and 200A to 200B.

Foliage description:

*Arrangement.*—Opposite, simple.

*Length.*—About 7.8 cm.

*Width.*—About 7.1 cm.

*Shape.*—Pinnatisect.

*Apex.*—Acute.

*Base.*—Attenuate.

*Margin.*—Pinnatifid.

*Texture, upper and lower surfaces.*—Smooth, glabrous.

*Venation.*—Pinnate.

*Color.*—Developing foliage, upper surface: 143A. Developing foliage, lower surface: 146B. Fully expanded foliage, upper surface: 137A; venation, 144C, towards the base, flushed with 176B. Fully expanded foliage, lower surface: 147B; venation, 148C.

*Petioles.*—Length: About 3.8 cm. Diameter: About 5 mm. Texture, upper and lower surfaces: Smooth, glabrous. Color, upper surface: 176B; wings, 143B to 143C. Color, lower surface: 147B flushed with 176B; wings, 143A.

Inflorescence description:

*Appearance.*—Single type inflorescence form with obovate-shaped ray florets. Inflorescences terminal and axillary and face mostly upright. Disc and ray florets arranged acropetally on a capitulum. Inflorescences moderately fragrant, pleasant.

*Flowering season.*—Plants flower from late spring to late summer in The Netherlands; flowering continuous during this period.

*Inflorescence longevity.*—Inflorescences last about ten days on the plant; inflorescences persistent.

*Quantity of inflorescences.*—Freely flowering habit, about nine inflorescences develop per lateral branch.

*Inflorescence bud.*—Height: About 1.1 cm. Diameter: About 1.2 cm. Shape: Globular. Color: Towards the base, 144A to 144B; towards the apex, between N186A and N186C.

*Inflorescence size.*—Diameter: About 4.4 cm. Depth (height): About 1.5 cm. Diameter of disc: About 4 mm. Receptacle diameter: About 4 mm. Receptacle height: About 2.5 cm.

*Ray florets.*—Shape: Obovate. Length: About 2.1 cm. Width: About 1.3 cm. Apex: Rounded. Base: Attenuate. Margin: Entire. Texture, upper and lower surfaces: Smooth, glabrous. Number of ray florets per inflorescence: About eight in about two whorls. Color: When opening and fully opened, upper surface: Slightly darker and more red than 187A. When opening and fully opened, lower surface: Close to 187A; towards the base, 187C to 187D.

*Disc florets.*—Arrangement: Massed at center of receptacle. Shape: Tubular, elongated. Apex: Acute. Length: About 1.1 cm. Diameter, apex: About 1.9 mm. Diameter, base: About 0.8 mm. Number of disc florets per inflorescence: About 60. Color, immature: Close to 200A. Color, mature: Towards the apex, close to 200A; mid-section, close to 2B to 2C; towards the base, close to 145C.

*Phyllaries.*—Number of phyllaries per inflorescence: About 20 arranged in two whorls. Length: About 9 mm. Width: About 2.5 mm. Shape: Obovate to elliptic. Apex: Acute. Base: Cuneate. Margin: Entire. Texture, upper and lower surfaces: Smooth, glabrous. Color, outer whorl, upper and lower surfaces: Between 143A and 147A. Color, inner whorl, upper and lower surfaces: 187B to 187C; towards the apex, 187A; towards the base, 145B.

*Peduncles.*—Length, terminal peduncle: About 6.6 cm. Diameter: About 2 mm. Angle: Mostly erect to about 30° from vertical. Strength: Strong, flexible. Texture: Smooth, glabrous. Color: 152A to 152B; towards the base, 177A to 177B; at the base, between N186C and 200A to 200B.

*Reproductive organs.*—Androecium: Present on disc florets only. Anther length: About 2 mm. Anther shape: Lanceolate. Anther color: 200A. Pollen amount: Moderate. Pollen color: 14A. Gynoecium: Present on both ray and disc florets. Pistil length: About 6 mm. Stigma shape: Two-parted. Stigma color: Between N186C to 200A. Style length: About 5 mm. Style color: 151B. Ovary color: 145C to 145D.

*Seed/fruit.*—Seed and fruit production has not been observed.

Disease/pest resistance: Plants of the new *Cosmos* have been observed to be relatively tolerant to Powdery Mildew. Resistance to pests and other pathogens common to *Cosmos* has not been observed on plants grown under commercial conditions.

Garden performance: Plants of the new *Cosmos* have been observed to have good garden performance and to tolerate wind, rain and temperatures from about −3° C. to about 40° C.

It is claimed:

1. A new and distinct *Cosmos* plant named 'New Choco' as illustrated and described.

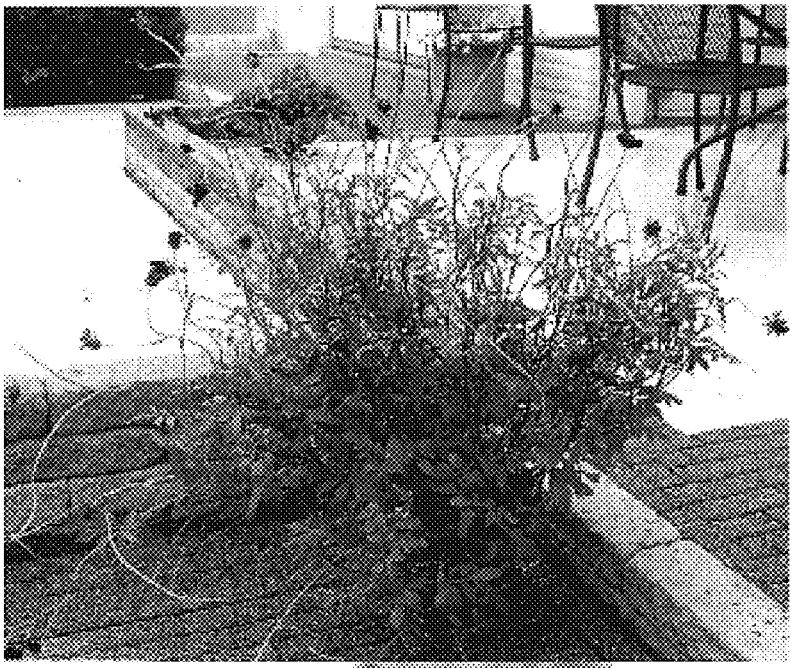
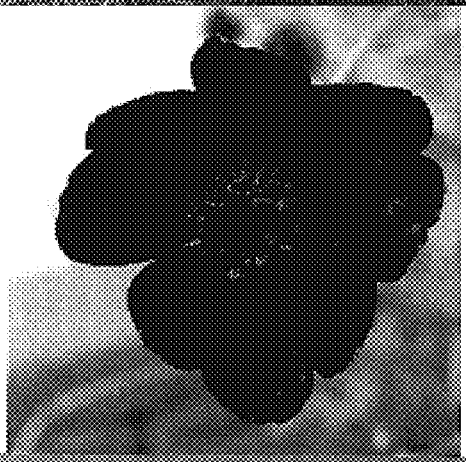
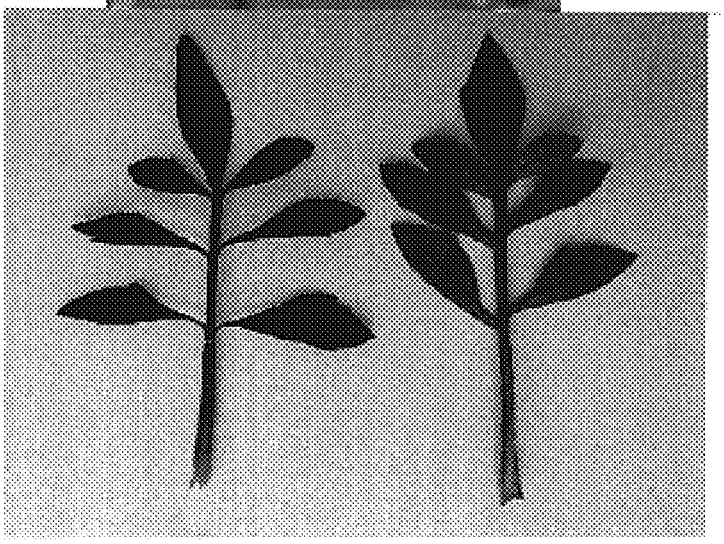

* * * * *